(12) United States Patent
Xu et al.

(10) Patent No.: US 11,986,330 B2
(45) Date of Patent: May 21, 2024

(54) METHOD AND SYSTEM FOR GENERATING OBJECT 3D POINT CLOUD IN MEDICAL IMAGING SYSTEM

(71) Applicant: GE Precision Healthcare LLC, Wauwatosa, WI (US)

(72) Inventors: Yanran Xu, Beijing (CN); Yu Huang, Beijing (CN); Fanbo Meng, Beijing (CN); Raghu Prasad, Beijing (CN); Adam G. Pautsch, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 390 days.

(21) Appl. No.: 16/890,304

(22) Filed: Jun. 2, 2020

(65) Prior Publication Data

US 2020/0390406 A1    Dec. 17, 2020

(30) Foreign Application Priority Data

Jun. 14, 2019 (CN) .......................... 201910514150.7

(51) Int. Cl.
*A61B 6/10* (2006.01)
*A61B 6/00* (2006.01)
(Continued)

(52) U.S. Cl.
CPC ............ *A61B 6/102* (2013.01); *A61B 6/0407* (2013.01); *A61B 6/547* (2013.01); *G06T 11/008* (2013.01);
(Continued)

(58) Field of Classification Search
CPC ......... A61B 5/055; A61B 6/032; A61B 6/037; A61B 6/0407; A61B 6/0487; A61B 6/102;
(Continued)

(56) References Cited

U.S. PATENT DOCUMENTS 9,811,902 B2    11/2017    Flohr
2014/0354637 A1*  12/2014    Reiner ...................... G06T 7/20
                                                                    345/420
(Continued)

OTHER PUBLICATIONS

Booij, Ronald, et al. "Accuracy of automated patient positioning in CT using a 3D camera for body contour detection." European Radiology 29 (2019): 2079-2088; first published online Oct. 10, 2018. (Year: 2018).*

(Continued)

*Primary Examiner* — Daniel F Hajnik (57) ABSTRACT

A method for generating an object 3D point cloud in a medical imaging system comprising a machine table and a scanning device comprises: extracting a valid 3D point cloud in a valid region where the machine table is located from a global 3D point cloud based on a current height of the machine table and boundary information of the machine table, wherein the global 3D point cloud comprises 3D point clouds of an object and a surrounding environment thereof, and the object 3D point cloud is comprised in the valid 3D point cloud; and removing an environment 3D point cloud of the surrounding environment from the valid 3D point cloud to obtain the object 3D point cloud, wherein the surrounding environment comprises at least part of the machine table. In some embodiments, a moving path of the machine table in the medical imaging system is planned using the object 3D point cloud. In some embodiments, collision prediction of the object is performed in the medical imaging system using the object 3D point cloud.

10 Claims, 9 Drawing Sheets

(51) Int. Cl.
  *A61B 6/03* (2006.01)
  *A61B 6/04* (2006.01)
  *G06T 11/00* (2006.01)
  *G06T 15/08* (2011.01)

(52) U.S. Cl.
  CPC .............. *G06T 15/08* (2013.01); *A61B 6/032* (2013.01); *G06T 2210/21* (2013.01); *G06T 2210/56* (2013.01)

(58) Field of Classification Search
  CPC ........... A61B 6/465; A61B 6/547; G06T 7/11; G06T 11/008; G06T 15/08; G06T 17/10; G06T 2200/08; G06T 2210/21; G06T 2210/56; G06T 2207/10028; G06T 2207/10088; G16H 30/20
  See application file for complete search history.

(56) References Cited

U.S. PATENT DOCUMENTS

| | | | |
|---|---|---|---|
| 2015/0213646 A1 | 7/2015 | Ma | |
| 2016/0306924 A1* | 10/2016 | Singh | G06F 16/51 |
| 2018/0228450 A1* | 8/2018 | Vega | A61B 6/545 |
| 2018/0330496 A1* | 11/2018 | Ma | A61B 6/032 |
| 2020/0205723 A1* | 7/2020 | Massey | G06T 7/0012 |

OTHER PUBLICATIONS

Gao, Xianz, Wei Hu, and Zongming Guo. "Graph-based point cloud denoising." 2018 IEEE Fourth International Conference on Multimedia Big Data (BigMM). IEEE, 2018. (Year: 2018).*

* cited by examiner

METHOD AND SYSTEM FOR GENERATING OBJECT 3D POINT CLOUD IN MEDICAL IMAGING SYSTEM

CROSS-REFERENCE TO RELATED APPLICATIONS

This application claims the benefit of Chinese Patent Application No. 201910514150.7 filed on Jun. 14, 2019, the disclosure of which is herein incorporated by reference in its entirety.

TECHNICAL FIELD

The present disclosure relates to an imaging technology, and in particular, to a method and system for generating an object 3D point cloud in a medical imaging system. The present disclosure further relates to a method and system for planning a moving path of a machine table in a medical imaging system, and further relates to a method for performing collision prediction of an object in a medical imaging system.

BACKGROUND

Computed tomography (CT) is an imaging method mainly used in medical diagnosis. In CT, an X-ray source and an X-ray detector working together with the X-ray source rotate around a machine table carrying a patient, and photographing is performed at different angular positions of the X-ray source and the X-ray detector. The machine table can move forward and backward along a rotation axis, which is also referred to as a system axis, and can move up and down in a height direction, so as to move the patient to a position required for scanning. Scanning information is processed after the scanning ends, so as to generate an X-ray image of three-dimensional (3D) tomography.

In conventional CT scanning, an operator uses laser projected on a patient's body to assist in positioning before the scanning starts. However, before this, the operator needs to manually operate a machine table to move the patient to a position where scanning can be performed. Since the positioning accuracy depends on the operator's experience, subjective errors of the operator may be introduced.

SUMMARY

The inventor has realized that if a 3D point cloud representing a three-dimensional contour of an object can be obtained before scanning starts, the 3D point cloud can be used to assist an operator in moving a machine table to a position where scanning can be performed, so as to reduce or eliminate manual operations of the operator and introduction of subjective errors. Therefore, the inventor desires to provide a method and system capable of generating an object 3d point cloud in a medical imaging system.

One aspect of the present disclosure provides a method for generating an object 3D point cloud in a medical imaging system, wherein the medical imaging system comprises: a machine table, for carrying a to-be-scanned object; and a scanning device, the scanning device having a scanning space allowing the machine table to enter therein, the method comprising: extracting a valid 3D point cloud in a valid region where the machine table is located from a global 3D point cloud based on a current height of the machine table and boundary information of the machine table, wherein the global 3D point cloud comprises 3D point clouds of the object and a surrounding environment thereof, and the object 3D point cloud is comprised in the valid 3D point cloud; and removing an environment 3D point cloud of the surrounding environment from the valid 3D point cloud to obtain the object 3D point cloud, wherein the surrounding environment comprises at least part of the machine table.

Another aspect of the present disclosure provides a method for planning a moving path of a machine table in a medical imaging system, wherein the medical imaging system comprises: the machine table, for carrying a to-be-scanned object; and a scanning device, the scanning device having a scanning space allowing the machine table to enter therein, the method comprising: determining a to-be-scanned region in an object 3D point cloud of the object based on a scanning plan; determining a center of gravity of the to-be-scanned region and a height of the center of gravity; determining a target height for positioning the machine table based on the height of the center of gravity and a central height of the scanning space, so that the height of the center of gravity is equal to the central height of the scanning space when the machine table is positioned at the target height; and planning the moving path of the machine table based on the determined target height, wherein the scanning plan comprises positioning information of the to-be-scanned region relative to the object.

Yet another aspect of the present disclosure provides a method for performing collision prediction of an object in a medical imaging system, wherein the medical imaging system comprises: a machine table, for carrying a to-be-scanned object; and a scanning device, the scanning device having a scanning space allowing the machine table to enter therein, the method comprising: judging whether an object 3D point cloud of the object overlaps a 3D point cloud of a surrounding environment during a moving process of moving in an advance/retreat direction of the machine table at a planned height of the machine table, so as to predict whether the object collides with the surrounding environment during the moving process.

BRIEF DESCRIPTION OF THE DRAWINGS

The embodiments discussed herein are illustrated generally by way of example rather than limitation in the drawings. In the drawings (these drawings are not necessarily drawn to scale), like numerals may describe similar components in different views.

DETAILED DESCRIPTION

Numerous specific details are set forth in the following description. However, it should be understood that embodiments of the present disclosure may be practiced without these specific details. In other examples, well-known circuits, structures, and techniques are not shown in detail so as not to obscure the understanding of the description.

References in the specification to "an embodiment," "embodiment," "exemplary embodiment," and so on indicate that the embodiment described may include a specific feature, structure, or characteristic, but the specific feature, structure, or characteristic is not necessarily included in every embodiment. Besides, such phrases do not necessarily refer to the same embodiment. Further, when a specific feature, structure, or characteristic is described in connection with an embodiment, it is believed that effecting such feature, structure, or characteristic in connection with other embodiments (whether or not explicitly described) is within the knowledge of those skilled in the art.

The embodiments of the present disclosure use depth image data to obtain an object 3D point cloud by computation. The disclosure is applicable not only to a human body, but also to any other object, such as a living entity other than humans and a non-living entity; the above are thus referred to as an "object" herein. In addition, the embodiments of the present disclosure further use an object 3D point cloud to plan a moving path of a machine table and predict whether an object collides with a surrounding environment (such as a scanning device) during the process of moving with the machine table.

The depth image data described herein may be captured by a depth camera, where the depth camera may be a structured light-based camera, a stereo camera, or a time-of-flight camera. The image data obtained from the depth camera is generally referred to as RGB-D (RGB+depth) data, which usually includes an RGB image (where each pixel has an RGB value) and a depth image (where the value of each pixel corresponds to a depth or a distance of the pixel from the camera). The present disclosure mainly uses the depth image.

Exemplary CT System

Figure 1:
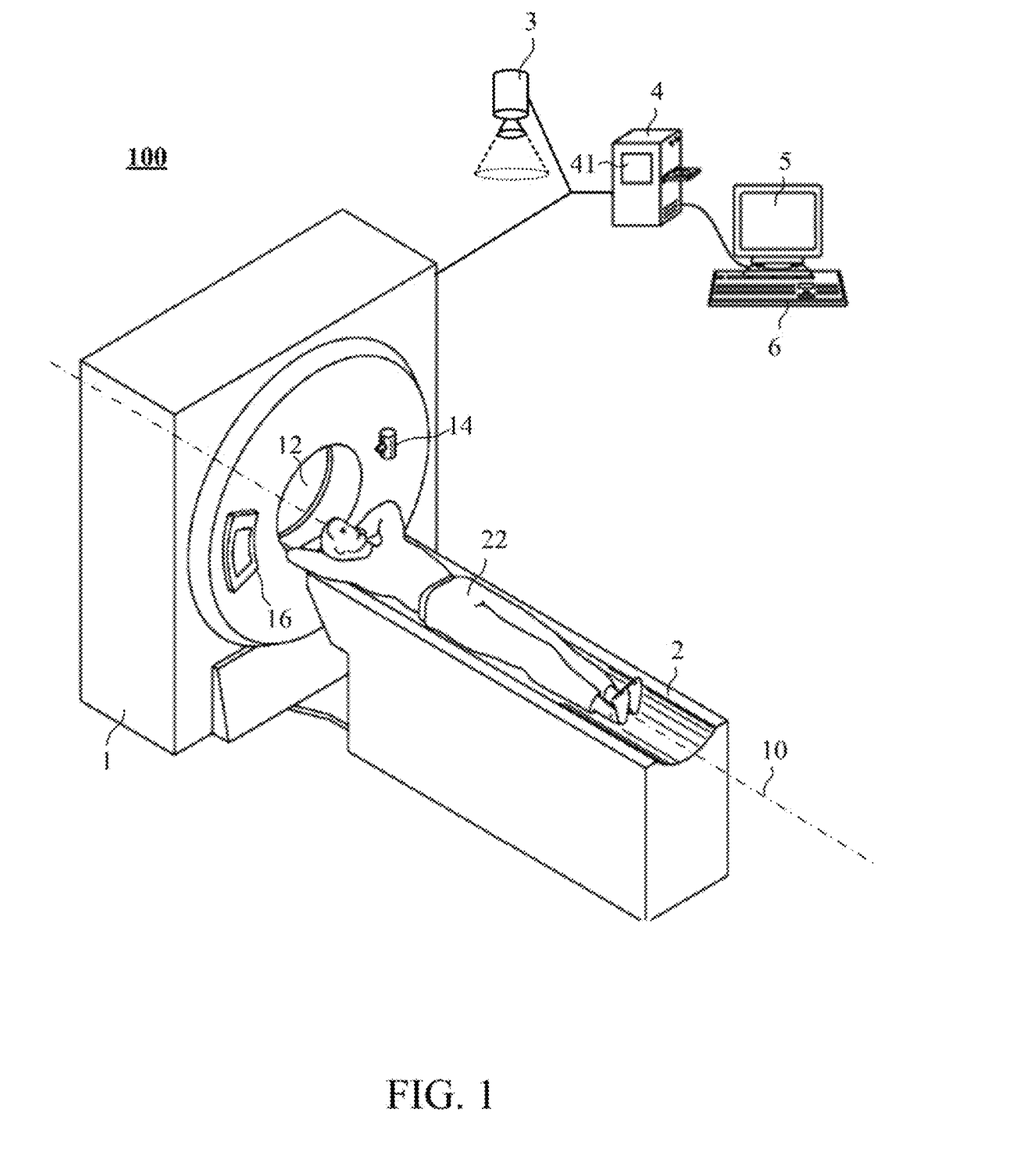
FIG. 1 is a schematic view of an exemplary medical imaging system, for example, a CT system 100, according to an embodiment.

FIG. 1 is a schematic view of an exemplary medical imaging system, for example, a CT system 100, according to an embodiment. The CT system 100 includes a scanning device 1 and a machine table 2. The scanning device 1 includes a scanning space 12 having a system axis 10, and an X-ray source 14 and an X-ray detector 16 arranged opposite to each other on two sides of the scanning space 12, where the X-ray detector 16 can detect X-rays emitted by the X-ray source 14. The machine table 2 is used for placing an object 22 thereon. That is, the machine table 2 carries the object 22. The machine table 2 can move forward and backward along the system axis 10 to enter the scanning space 12 of the scanning device 1. The machine table 2 can be raised and lowered in a height direction, namely, a direction perpendicular to the ground, so that the scanning object can get on and off the machine table 2 conveniently. In the case of capturing an X-ray image (referred to as "scanning" hereinafter), the machine table 2 enters the scanning space 12 while carrying the object 22, the X-ray detector 16 and the X-ray source 14 may rotate around the system axis 10 or remain still, and the X-ray detector 16 receives X-rays emitted by the X-ray source 14 and passing through the object 22 located in the scanning space 12 to perform imaging.

In some embodiments, the CT system includes at least one depth camera 3, which is designed to photograph at least one part of the surface of the object 22 without contact and to output depth image data. In some embodiments, the depth camera 3 is installed on a ceiling of a room (scanning room) so as to reduce the blind area in the field of view (FOV). In some embodiments, the depth camera 3 may be centrally positioned above the object 22 or centrally positioned above the machine table 2. In this way, the quality of depth information about the object 22 and the quality of a generated 3D point cloud of the object 22 can be as uniform as possible. In some embodiments, the depth camera 3 may be installed or integrated in or on the scanning device 1. In some embodiments, the depth camera 3 may be integrated in a rotatable part of the scanning device 1 so that the depth camera 3 can rotate with the X-ray source 14 and the X-ray detector 16, and thus can photograph the object 22 at different angles. In some embodiments, the depth camera 3 may be installed on a positioning device such as a tripod.

In some embodiments, the CT system includes a computing apparatus 4 which includes a processor 41, where the processor 41 is configured to perform the methods described in the embodiments of the present disclosure. In some embodiments, the computing apparatus 4 is designed to load a computer program into an internal memory thereof. The computer program includes commands readable by the computing apparatus 4 and is an integral part of a computing program product. The computer program product may be stored, for example, in a computer-readable medium. The instructions of the computer program readable by the computing apparatus 4 are designed to implement the methods according to the present disclosure when the instructions are executed by the processor 41 of the computing apparatus 4.

The computer-readable medium may include, but not limited to, a non-transitory, tangible arrangement of an article manufactured or formed by a machine or apparatus, including a storage medium such as the following: a hard disk; any other type of disk including a floppy disk, an optical disk, a compact disk read-only memory (CD-ROM), a compact disk rewritable (CD-RW), and a magneto-optical disk; a semiconductor device such as a read-only memory (ROM), a random access memory (RAM) such as a dynamic random access memory (DRAM) and a static random access memory (SRAM), an erasable programmable read-only memory (EPROM), a flash memory, and an electrically erasable programmable read-only memory (EEPROM); a phase change memory (PCM); a magnetic or optical card; or any other type of medium suitable for storing electronic instructions.

The computing apparatus 4 is connected to an output unit 5 for displaying various information. The output unit 5 is, for example, an LCD (LCDs) or a plasma or OLED display(s). In some embodiments, the output unit 5 may be installed or integrated on the scanning device 1. In addition, the computing apparatus 4 is connected to an input unit 6. The input unit 6 is, for example, configured to input information, such as control instructions and a scanning plan, through user interaction. The input unit 6 is, for example, a keyboard, a mouse, a touch screen, or a microphone for voice input. In some embodiments, the scanning device 1 includes a control panel, where the control panel may include a flat-panel display as the output unit 5 and keys as the input unit 6, and the control panel may also be a flat-panel display having a touch screen.

The computing apparatus 4 is connected to the depth camera 3 and the scanning device 1, so that depth image data of the object 22 obtained by the depth camera 3, scanning data of the scanning device 1, and real-time position information of the CT system 100 can be transferred to the computing apparatus 4, where the real-time position information of the CT system 100 includes current position information of various parts of the system, such as a current height of the machine table 2 and boundary information of the machine table 2. In addition, the computing apparatus 4 can send instructions to the scanning device 1 and the machine table 2 so as to control movement of the machine table 2 and scanning of the scanning device 1.

Examples of the CT system have been described above, but it should be understood that the methods of the present disclosure also apply to other medical imaging systems, such as an XR (X-ray photography) system, a PET (positron emission tomography) system, or an MR (magnetic resonance imaging) system.

Exemplary Method for Generating Object 3D Point Cloud

Figure 2:
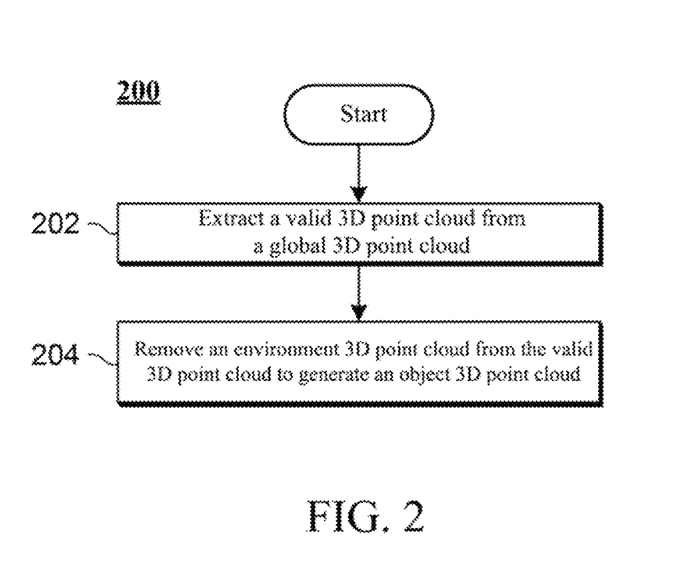
FIG. 2 is a flowchart of a method 200 for generating an object 3D point cloud according to an embodiment.

FIG. 2 is a flowchart of a method 200 for generating an object 3D point cloud according to an embodiment.

The method in this embodiment as a whole includes extracting a valid 3D point cloud of a valid region where the machine table 2 is located from a global 3D point cloud including 3D point clouds of the object 22 and a surrounding environment thereof, and then removing an environment 3D point cloud of the surrounding environment from the valid 3D point cloud to obtain an object 3D point cloud. Thus, the object 3D point cloud can be generated from the global 3D point cloud including the object 22 and the surrounding environment thereof.

Specifically, the method in this embodiment starts at step 202: extract a valid 3D point cloud in a valid region where the machine table 2 is located from a global 3D point cloud based on a current height of the machine table 2 and boundary information of the machine table 2, where the global 3D point cloud includes 3D point clouds of the object 22 and a surrounding environment thereof, and the object 3D point cloud is included in the valid 3D point cloud.

The current height of the machine table 2 may be obtained from real-time position information of the CT system 100. The boundary information of the machine table 2 is used for determining a rough contour of the machine table 2. In some embodiments, the boundary information of the machine table 2 may be position information, such as coordinates, of four corners of the machine table 2. It should be noted that the machine table 2 is not required to be a strict rectangle in this case, where the corners may be corners of an external quadrangle of the machine table 2.

In some embodiments, the global 3D point cloud may be obtained in the following manner: converting depth image data including the object 22 and a surrounding environment thereof that is captured using the depth camera 3, so as to obtain a global 3D point cloud including the object 22 and the surrounding environment thereof. As described above, the depth camera 3 can output RGB image data and depth image data, and the depth image data is used here. In other embodiments, the depth image data may be obtained by an independent photographing system and transferred to the computing apparatus 4 in a wired or wireless manner.

The depth image data may be converted into point cloud information, namely, the global 3D point cloud, by a well-known method. In some embodiments, the global 3D point cloud may be converted from a coordinate system (for example, a camera coordinate system) of its own to a coordinate system of the CT system 100. Since the boundary information of the machine table 2 is obtained from the real-time position information of the CT system 100, the coordinate system of the CT system 100 is also used as a reference. Therefore, the global 3D point cloud and the boundary information of the machine table 2 can be processed in the same coordinate system to extract the valid 3D point cloud. In other embodiments, the boundary information of the machine table 2 may be converted from the coordinate system of the CT system 100 to the coordinate system, such as, the camera coordinate system, of the global 3D point cloud, and then the global 3D point cloud and the boundary information of the machine table 2 are processed in the same coordinate system to extract the valid 3D point cloud. Certainly, the boundary information of the machine table 2 and the global 3D point cloud may also be converted to other coordinate systems for processing, as long as reference coordinate systems thereof are the same.

The valid region described herein may be a three-dimensional region including at least part of the machine table 2 and the object 22 carried thereon. In some embodiments, the valid region may be a three-dimensional region having a carrying surface of the machine table 2 as a bottom surface. A height dimension of the valid region may be any height dimension not less than a thickness of the object 22, so as to include the entire object 22 therein. In some embodiments, the entire region above the carrying surface of the machine table 2 may be used as the valid region. In some embodiments, the valid region may be rectangular.

A length (in a length direction of the machine table 2) and a width (in a width direction of the machine table 2) of the valid region may be determined based on a length and a width of the machine table 2 or the external quadrangle thereof. In some embodiments, the length and width of the valid region may be approximately equal to the length and width of the machine table 2 or the external quadrangle thereof, respectively. In some embodiments, the length and width of the valid region may be greater than the length and width of the machine table 2 or the external quadrangle thereof, respectively.

Figure 3:
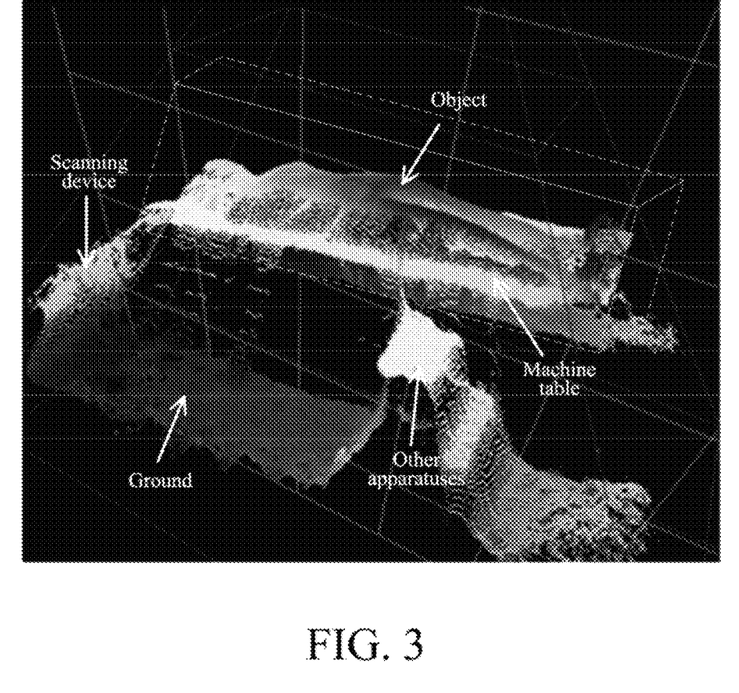
FIG. 3 illustrates an exemplary global 3D point cloud and an exemplary valid region according to an embodiment.

FIG. 3 illustrates an exemplary global 3D point cloud and an exemplary valid region according to an embodiment. As shown in FIG. 3, a global 3D point cloud converted from depth image data includes all information in the field of view of the depth camera 3, namely, 3D point clouds of the object 22 and a surrounding environment thereof. The surrounding environment includes, for example, at least part of the scanning device 1, the machine table 2, the ground and/or other apparatuses, as shown in FIG. 3. Step 202 is performed so that a valid 3D point cloud of a valid region represented by, for example, dashed lines in FIG. 3 can be extracted from the global 3D point cloud. It should be understood that the valid region in FIG. 3 is merely an example, and can be arbitrarily changed within the scope of the present disclosure.

Although the valid 3D point cloud extracted by performing step 202 has most environment 3D point clouds (such as a 3D point cloud of the ground and most 3D point clouds of the scanning device 1 and other apparatuses) removed therefrom, the valid 3D point cloud still includes some environment 3D point clouds, such as a 3D point cloud of the machine table 2 and some 3D point clouds of the scanning device 1.

Accordingly, step 204: further remove these environment 3D point clouds from the valid 3D point cloud to obtain an object 3D point cloud.

The information (such as shape, position, and state) of the surrounding environment is known, and thus a 3D point cloud of the surrounding environment is also known. In some embodiments, the environment 3D point cloud may be pre-stored in the computing apparatus 4. In some embodiments, surrounding environments not carrying the object 22 may be photographed using the depth camera 3 at the same position and orientation to obtain environment 3D point clouds of the surrounding environments. Here, it should be understood that the step of photographing the surrounding environment does not need to be performed each time an object 3D point cloud is generated; the step may be performed once after the CT system 100 and the depth camera 3 have been installed and the obtained environment 3D point cloud may be saved, and then the environment 3D point cloud may be invoked each time an object 3D point cloud is generated. In addition, the photographing may also be performed whenever the environment changes (for example, when an apparatus moves in position or when other apparatuses are added). In some embodiments, the environment 3D point cloud may also be generated by computing and sampling according to real-time position information of the CT system 100.

Figure 4:
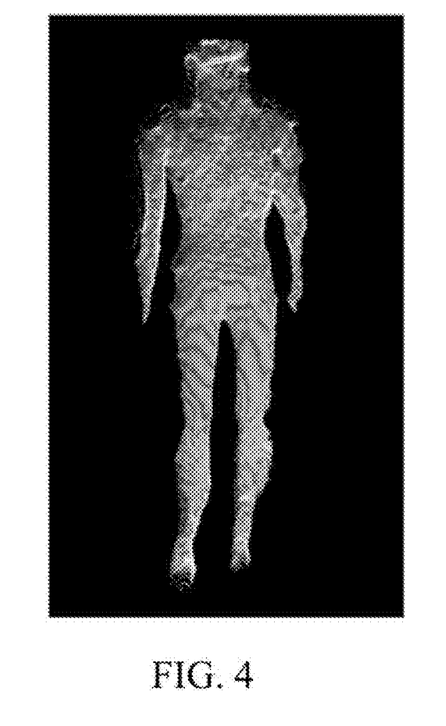
FIG. 4 illustrates an example of an object 3D point cloud according to an embodiment.
Figure 5:
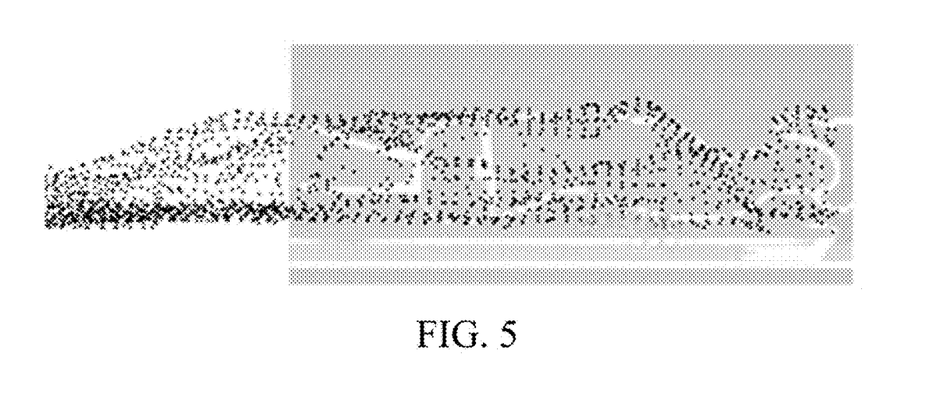
FIG. 5 illustrates comparison between the object 3D point cloud according to the embodiment and a DICOM image captured using a scanning apparatus.

FIG. 4 illustrates an example of an object 3D point cloud generated through step 204, and FIG. 5 illustrates comparison between the object 3D point cloud and a DICOM (Digital Imaging and Communications in Medicine) image captured using a scanning apparatus (the X-ray source 14 and the X-ray detector 16). As shown in FIG. 4, the object 3D point cloud seldom includes any environment 3D point cloud, and can clearly reflect structural features of the object 22. In FIG. 5, the dotted pattern represents the object 3D point cloud described herein, and the solid white lines represent the DICOM image described above. As can be seen from FIG. 5, the object 3D point cloud generated using the method in this embodiment highly matches the actually captured DICOM image of the object, and the object 3D point cloud reflects structural information of the object 22. Moreover, the method 200 in this embodiment does not need to generate a model of the object to match a preset model, and thus can be applied to various objects not just human bodies.

In some cases, some part(s) of the object 22 may exceed the boundary of the machine table 2, for example, because of the position, posture, or the like of the object 22 relative to the machine table 2. In order to retain the complete object 3D point cloud, the length and width of the valid region (the part indicated by dashed lines in FIG. 3) may be further increased to prevent removal of this part. In some embodiments, the width of the valid region may be increased from the width of the machine table 2 (or the external quadrangle thereof) to a maximum width of the scanning space 12. In addition, in some cases, an additional mechanism may be provided on the machine table 2 and at least part of the object 22 may be carried on the additional mechanism. If the valid region is set using the length of the machine table 2, the object 3D point cloud on the additional mechanism may be removed. Accordingly, in some embodiments, the length of the valid region may be further increased on the basis of the length of the machine table 2.

In some embodiments, noise reduction processing may be performed on the object 3D point cloud. The noise reduction processing may include executing a filtering and clustering algorithm. Filtering may be, for example, Gaussian filtering or moving average filtering, for smoothing the object 3D point cloud. Clustering may be implemented, for example, using a function in a PCL (Point Cloud Library). All points will be clustered into several classes, and then points of noise class (for example, the scanning device 1 and the machine table 2) are deleted.

In some embodiments, downsampling voxelization may be performed on the object 3D point cloud to obtain better computing performance.

In some embodiments, a structural model (for example, a mesh model) of the object may be further generated based on the object 3D point cloud to match a preset model in the system.

Figure 6:
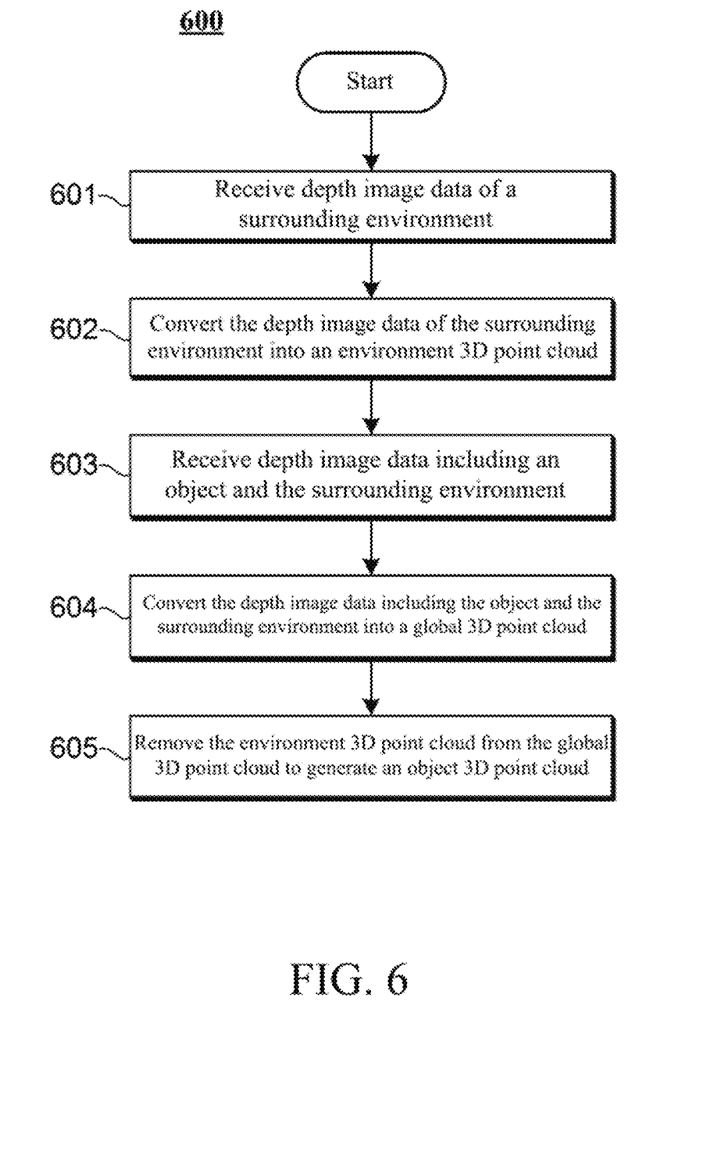
FIG. 6 is a flowchart of a method 600 for generating an object 3D point cloud according to another embodiment.

FIG. 6 is a flowchart of a method 600 for generating an object 3D point cloud according to another embodiment. The method 600 in this embodiment differs from the method 200 shown in FIG. 2 in that the method 600 entails first acquiring an environment 3D point cloud not including the object 22, and then removing the environment 3D point cloud from a global 3D point cloud without extracting a valid 3D point cloud.

Specifically, the method in this embodiment starts at step 601: before the machine table 2 carries the object 22, first, the computing apparatus 4 receives depth image data of a surrounding environment not including the object 22. The depth image data may be obtained as described above, for example, captured by the depth camera 3. Next, step 602: convert the depth image data received in step 601 into an environment 3D point cloud.

Then, step 603: after the object 22 is carried on the machine table 2, capture a depth image including the object 22 and the surrounding environment thereof by the depth camera 3 at the same position and orientation as those for capturing a depth image of the surrounding environment in step 601, and then transfer depth image data to the computing apparatus 4. Afterwards, step 604: convert the depth image data received in step 603 into a global 3D point cloud.

Because of the same camera position and orientation for capturing depth images in step 601 and step 603, an environment 3D point cloud included in the global 3D point cloud may be considered the same as the environment 3D point cloud obtained in step 601.

Thus, in step 605, the environment 3D point cloud obtained through step 602 may be directly removed from the global 3D point cloud to generate the object 3D point cloud.

The object 3D point cloud generated by the methods 200 and 600 described in the embodiments of the present disclosure enables an operator to intuitively and accurately grasp contour information of the object 22, and the object 3D point cloud can be further used to assist in subsequent scanning.

Exemplary Method for Planning Moving Path of Machine Table

Figure 7:
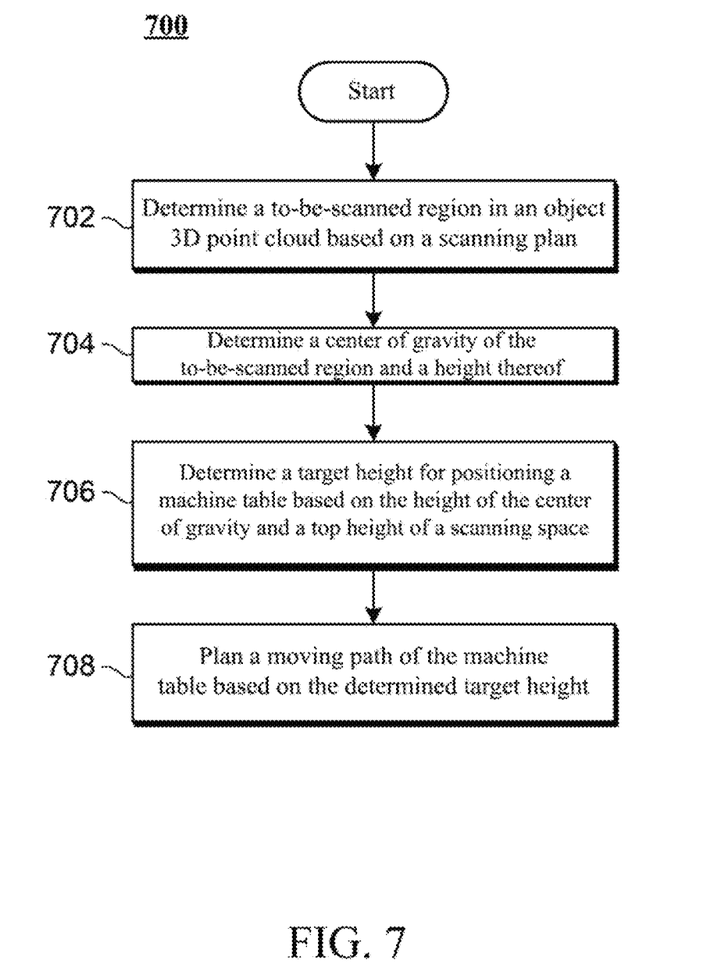
FIG. 7 is a flowchart of a method 700 for planning a moving path of a machine table 2 in a medical imaging system described herein according to an embodiment.

FIG. 7 is a flowchart of a method 700 for planning a moving path of a machine table in a medical imaging system described herein according to an embodiment.

The movement of the machine table 2 mainly includes two parts: bed lifting and bed shifting. Bed lifting refers to adjusting the machine table from an initial position to a certain height, and bed shifting refers advancing or retreating the machine table to a certain position along the system axis 10. The planning of the moving path of the machine table described herein refers to determining a target height at which the machine table needs to be positioned for scanning and planning the moving path of the machine table accordingly.

Specifically, the method in this embodiment starts at step 702: determine a to-be-scanned region in an object 3D according to a scanning plan.

The object 3D point cloud may be generated using the method described in the embodiment of the present disclosure, or may be obtained in other manners, such as converting an object contour model obtained by laser scanning into an object 3D point cloud.

The to-be-scanned region may be all or part of the object, such as the chest or head of the human or other parts indicated using positioning information. In some embodiments, the scanning plan may be input by an operator to the computing apparatus 4, for example, including positioning information of a to-be-scanned part relative to the object and photographing parameters of a precise flow required for scanning. In some embodiments, the positioning information represents a position of the to-be-scanned region relative to the object. In another embodiment, the positioning information is boundary landmarks representing a boundary of the to-be-scanned region. In the case that the object is an animate living entity, the boundary landmarks may be anatomical landmarks of the object, such as landmarks of joints, including left and right eyes, left and right knees, left and right side waists, groins, left and right wrists, left and right elbows, left and right shoulder tips, chest center, head bottom, head top, and the like.

Step 704: determine a center of gravity of the to-be-scanned region and a height of the center of gravity.

Next, step 706: determine a target height for positioning the machine table based on the height of the center of gravity of the to-be-scanned region and a central height of the scanning space 12 of the scanning device 1, so that the height of the center of gravity of the to-be-scanned region is equal to the central height of the scanning space 12 when the machine table 2 is positioned at the target height. Here, the height of the center of gravity and the central height may use the machine table 2 as the reference, or may use the ground as the reference, The determined target height will ensure that the to-be-scanned region is in the center of the scanning space 12.

Finally, step 708: plan the moving path of the machine table 2 based on the target height determined through step 706. Specifically, the machine table 2 may be raised or lowered from an initial height position to the target height, where the initial height position is, for example, a height position for carrying the object 22 on the machine table 2.

By means of the method 700 described in this embodiment, a moving path of the machine table 2 required for executing a scanning plan can be automatically planned according to an object 3D point cloud and the scanning plan, so that manual operations can be avoided.

In some embodiments, a maximum depth for the machine table 2 to enter the scanning device 1 to execute the scanning plan may be further determined based on a position of the boundary of the to-be-scanned region on an advance/retreat route of the machine table (the system axis 10) and a scanning range of the scanning device 1. The boundary position of the to-be-scanned region may be determined based on the positioning information of the to-be-scanned part included in the scanning plan. Thus, the moving path of the machine table 1 in an advance/retreat direction thereof (the system axis 10) may be further planned based on the maximum depth.

Exemplary Method for Collision Prediction of Scanning

Figure 8:
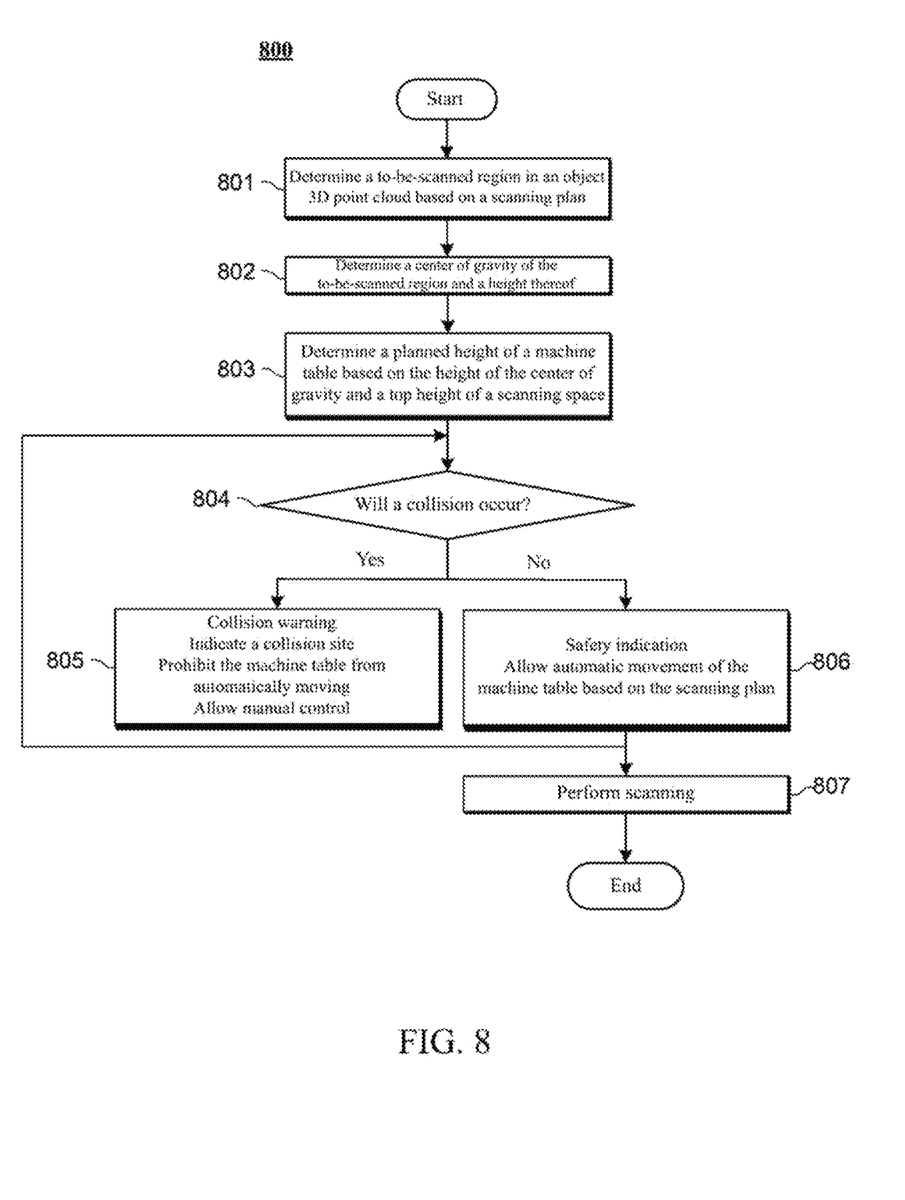
FIG. 8 is a flowchart of a method 800 for performing collision prediction of an object 22 in a medical imaging system described herein according to an embodiment.

FIG. 8 is a flowchart of a method 800 for performing collision prediction of an object 22 in a medical imaging system described herein according to an embodiment. In the method in this embodiment, it is predicted, according to a planned height of the machine table 2, whether the object 22 collides with a surrounding environment during the process of moving forward and backward with the machine table 2 at the planned height. The planned height of the machine table may be obtained based on the exemplary method for planning a moving path of a machine table described herein.

The method 800 in this embodiment starts at step 801: determine a to-be-scanned region in an object 3D according to a scanning plan.

The object 3D point cloud may be generated using the method described in the embodiment of the present disclosure, or may be obtained in other manners, such as converting an object contour model obtained by laser scanning into an object 3D point cloud.

The to-be-scanned region may be all or part of the object, such as the chest or head of the human or other parts indicated using positioning information. In some embodiments, the scanning plan includes positioning information of a to-be-scanned part. In some embodiments, the positioning information represents a position of the to-be-scanned region relative to the object. In another embodiment, the positioning information is boundary landmarks representing a boundary of the to-be-scanned region. In the case that the object is an animate living entity, the boundary landmarks may be anatomical landmarks of the object, such as landmarks of joints, including left and right eyes, left and right knees, left and right side waists, groins, left and right wrists, left and right elbows, left and right shoulder tips, chest center, head bottom, head top, and the like.

Step 802: determine a center of gravity of the to-be-scanned region and a height of the center of gravity.

Next, step 803: determine a target height for positioning the machine table as a planned height based on the height of the center of gravity of the to-be-scanned region and a central height of the scanning space 12 of the scanning device 1, so that the height of the center of gravity of the to-be-scanned region is equal to the central height of the scanning space 12 when the machine table 2 is positioned at the target height. Here, the height of the center of gravity and the central height may use the machine table 2 as the reference, or may use the ground as the reference, The determined target height will ensure that the center of gravity of the to-be-scanned region is in the center of the scanning space 12.

Next, step 804: judge whether the object 3D point cloud of the object 22 overlaps an environment 3D point cloud during a moving process of moving in an advance/retreat direction of the machine table 2 (the system axis 10) at the planned height of the machine table 2 that is determined through step 803, so as to predict whether the object 22 collides with a surrounding environment during the moving process.

The environment 3D point cloud is known as described above or may be captured by the depth camera.

When it is predicted in step 804 that the object 22 does not collide with the surrounding environment while moving with the machine table 2, the flow enters step 805. In step 805: an indication indicating that the object can safely move to a scanning position and does not collide with the surrounding environment during the scanning process, namely, a safety indication, may be presented to an operator. The safety indication may be displayed, for example, by means of a text, an image, or an animation, which is not limited in the present application.

Figure 9:
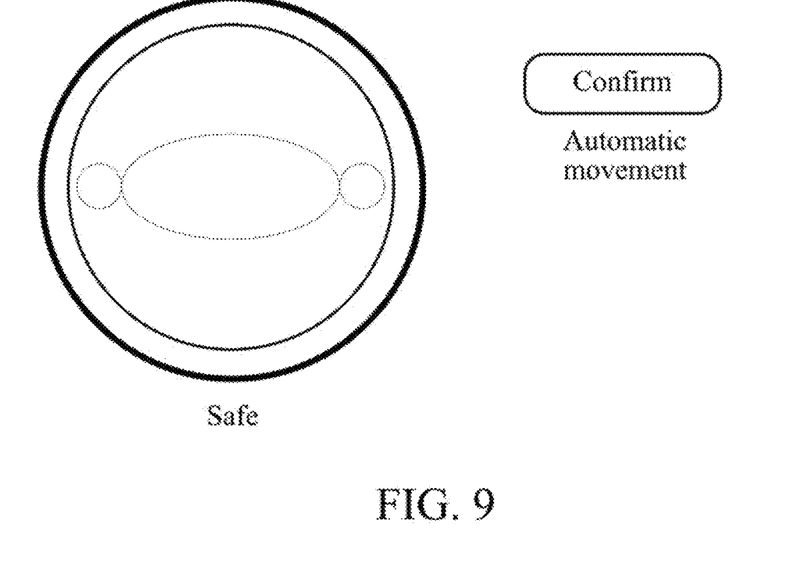
FIG. 9 illustrates an exemplary interface including a safety indication according to an embodiment.

FIG. 9 illustrates an exemplary interface including a safety indication according to an embodiment. The safety indication may be presented, for example, in a man-machine interaction interface of the output unit 5. As shown in FIG. 9, the thick solid line on the outer side represents the scanning space 12, the thin solid line on the inner side represents a boundary of a safe region where no collision occurs, and the pattern within the thin solid line is a simulated image of the object 22. Therefore, it is self-evident that a safety margin may be added when predicting a collision, namely, judging whether the object 3D point cloud overlaps the environment 3D point cloud during the moving process. In addition, the simulated image of the object 22 may be generated, for example, according to the object 3D point cloud in real time. For example, the simulated image of the object 22 is an image obtained by observing the object 3D point cloud along the system axis 10.

Since it is predicted that the object 22 does not collide with the surrounding environment while moving with the machine table 2, it can be observed in the interface shown in FIG. 9 that all parts of the object are located in the circle represented by the thin solid line and a safety indication is presented in the interface. The operator can accordingly judge that no collision occurs and an automatic movement function of the CT system 100 can be used so that the machine table 2 automatically moves according to a scanning plan to perform scanning. In the interface shown in FIG. 9, the button used for confirming automatic movement of the machine table is in an activated state so as to allow the operator to enable the automatic movement function. It should be understood that the interface shown in FIG. 9 is merely an example, and various display components may be designed according to needs. In addition, the interface shown in FIG. 9 may be displayed on the output apparatus 5, the control panel of the scanning device 1, or both.

After the operator confirms automatic movement and scanning is performed at the planned height in step 807, the flow ends.

Figure 10:
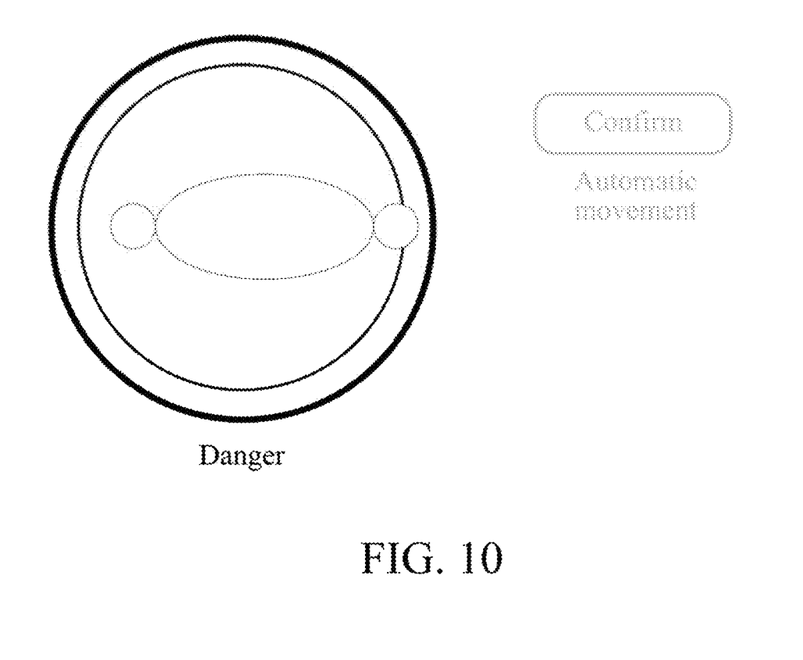
FIG. 10 illustrates an exemplary interface including a collision warning according to an embodiment.

When it is predicted in step 804 that the object 22 will collide with the surrounding environment while moving with the machine table 2, the flow enters step 805. Step 805: present a collision warning indicating a collision risk to the operator. The collision warning may be displayed, for example, by means of a text, an image, or an animation, which is not limited in the present application. FIG. 10 illustrates an exemplary interface including a collision warning according to an embodiment. Since it is predicted that the object 22 will collide with the surrounding environment, as shown in FIG. 10, part of the object is presented as going beyond the safety boundary represented by the thin solid line, and a "Danger" warning is displayed. In this case, automatic movement of the machine table 2 is prohibited, and the position of the object 22 needs to be changed to eliminate collision risks or the operator needs to manually control the movement of the machine table 2. Thus, the button used for confirming automatic movement of the machine table 2 in the interface shown in FIG. 10 changes to a disabled state.

In some embodiments, the interfaces shown in FIG. 9 and FIG. 10 change in real time according to the prediction result in step 804, so that the operator can intuitively know the result of collision prediction in real time.

Figure 11:
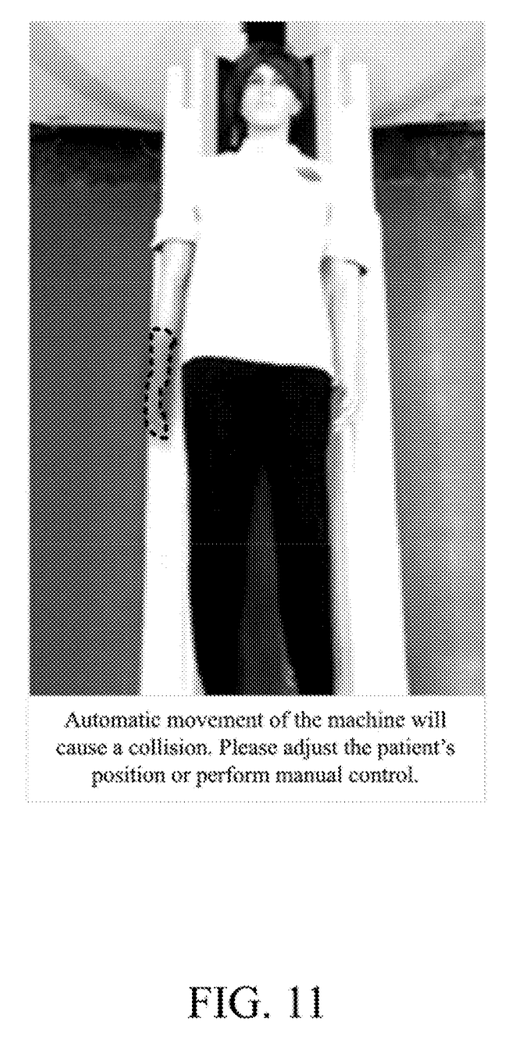
FIG. 11 illustrates an exemplary interface indicating a predicted collision site according to an embodiment.

In some embodiments, a site predicted to have a collision may further be presented in the man-machine interaction interface. FIG. 11 illustrates an exemplary interface indicating a predicted collision site according to an embodiment, where a site of the object that will have a collision with, for example, the scanning device 1 is further illustrated, which is the right hand indicated by dashed lines in the figure. This helps the operator to quickly identify a site having a collision risk so as to adjust the position, posture, or the like of the object to eliminate the collision risk. The collision site is a site corresponding to a part of the object 3D point cloud judged in step 804 to overlap the environment 3D point cloud during the moving process. In some embodiments, information is displayed in the interface for reminding the operator of a collision risk and recommend adjusting the object position or performing manual control. In some embodiments, the interface corresponds to the prediction result in step 804 in real time. In some embodiments, the part predicted to have a collision is highlighted in a manner different from other parts, which is not limited in any way herein. In some embodiments, a degree of collision is further judged according to an overlapping degree of the object 3D point cloud with the environment 3D point cloud during the moving process, so as to present the site predicted to have the collision in the man-machine interaction interface in a manner corresponding to the degree of collision. For example, the greater the degree of collision, the more strikingly the site predicted to have the collision is presented.

It should be noted that the collision risk prediction shown in step 804 is periodically performed. Once the collision risk is eliminated by adjusting the position, posture, or the like of the object, the flow enters step 806. On the contrary, even if it has been determined that no collision risk exists, in the case that a collision risk is regenerated due to a change of the position, posture, or the like of the object before scanning starts, the flow will enter step 805 via step 804, and a collision warning will be issued.

In addition, in the method 800 shown in FIG. 8, the planned height of the machine table 2 is obtained by performing step 802 and step 803. In other embodiments, the current height of the machine table 2 may also be used as the planned height without planning the moving path of the machine table 2.

In addition, in the method 800 shown in FIG. 8, collision prediction is performed based on the planned height of the machine table 2. However, the following situation may exist: assuming that the position and posture of the object 22 do not change, a collision risk may exist when scanning is performed on the entire object 22, but no collision risk may exist when scanning is performed on only part of the object 22. This is because the to-be-scanned region determined according to the scanning plan varies. Thus, in some embodiments, a moving range of the machine table 2 in the advance/retreat direction (the system axis 10) during the moving process based on a position of a boundary of the to-be-scanned region on the advance/retreat route of the machine table 2 (the system axis 10) and a scanning range of the scanning device 1. In this way, when collision prediction is performed, the moving range of the machine table 2 in the advance/retreat direction (the system axis 10) can be determined based on the scanning plan, so that a more accurate collision prediction result can be obtained.

Exemplary Computing Apparatus

Figure 12:
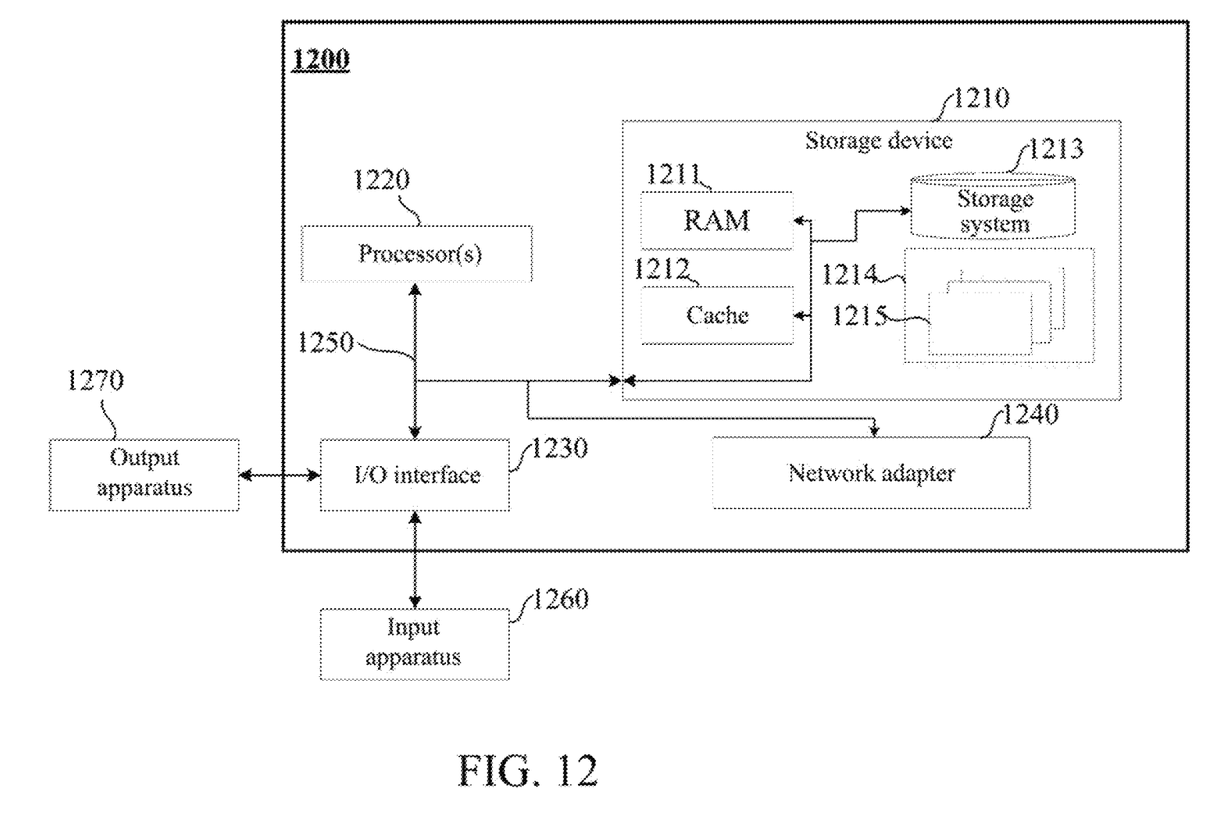
FIG. 12 is a block diagram of an exemplary computing apparatus according to an embodiment.

FIG. 12 is a block diagram of an exemplary computing apparatus 1200 according to an embodiment. The computing apparatus 1200 may be, for example, a personal computer (PC), a portable computer, a tablet apparatus, a workstation, or any machine capable of executing instructions that specify actions to be taken by that machine (in order or in other manners). In some embodiments, the computing apparatus 1200 includes, for example, one or a plurality of processors 1220; and a storage device 1210, configured to store one or a plurality of programs, where when the one or plurality of programs are executed by the one or plurality of processors 1220, the one or plurality of processors 1220 are caused to implement the methods described in the embodiments of the present disclosure. The processor is, for example, a digital signal processor (DSP), a microcontroller, an application-specific integrated circuit (ASIC), or a microprocessor.

The computing apparatus 1200 shown in FIG. 12 is merely an example, and should not cause any limitation to the function and use scope of the embodiments of the present disclosure.

As shown in FIG. 12, the components of the computing apparatus 1200 may further be connected to a bus 1250 connecting different system components (including the storage device 1210 and the processor 1220).

The bus 1250 represents one or a plurality of types of bus structures, including a memory bus or a memory controller, a peripheral bus, an accelerated graphics port, a processor, or a local bus using any bus structure in the plurality of bus structures. For example, these architectures include, but not limited to, an Industrial Standard Architecture (ISA) bus, a Micro Channel Architecture (MAC) bus, an enhanced ISA bus, a Video Electronics Standards Association (VESA) local bus, and a Peripheral Component Interconnect (PCI) bus.

The computing apparatus 1200 typically includes a plurality of computer system readable media. These media may be any available medium that can be accessed by the computing apparatus 1200, including volatile and non-volatile media as well as movable and non-movable media.

The storage device 1210 may include a computer system readable medium in the form of a volatile memory, for example, a random access memory (RAM) 1211 and/or a cache memory 1212. The computing apparatus 1200 may further include other movable/non-movable, and volatile/non-volatile computer system storage media. Only as an example, a storage system 1213 may be used to read/write a non-movable, non-volatile magnetic medium (not shown in FIG. 12, often referred to as a "hard disk drive"). Although not shown in FIG. 12, a magnetic disk drive used for reading/writing a movable non-volatile magnetic disk (for example, a "floppy disk") and an optical disk drive used for reading/writing a movable non-volatile optical disk (for example, a CD-ROM, a DVD-ROM, or other optical media) may be provided. In these cases, each drive may be connected to the bus 1250 via one or a plurality of data medium interfaces. The storage device 1210 may include at least one program product which has a group of program modules (for example, at least one program module) configured to execute the functions of the embodiments of the present disclosure.

A program/utility tool 1214 having a group of program modules (at least one program module) 1215 may be stored in, for example, the storage device 1210. Such a program module 1215 includes, but is not limited to, an operating system, one or a plurality of applications, other program modules, and program data. It is possible for each one or a certain combination of these examples to include implementations of a network environment. The program module 1215 typically executes the function and/or method in any embodiment described in the present disclosure.

The computing apparatus 1200 may also communicate with one or a plurality of input apparatuses 1260 (for example, a keyboard and a pointing apparatus) and output apparatuses 1270 (for example, a display), may also communicate with one or a plurality of apparatuses enabling a user to interact with the computing apparatus 1200, and/or communicate with any apparatus (for example, a network card or a modem) enabling the computing apparatus 1200 to communicate with one or a plurality of other computing apparatuses. Such communication may be carried out via an input/output (I/O) interface 1230. Moreover, the computing apparatus 1200 may also communicate with one or a plurality of networks (for example, a local area network (LAN), a wide area network (WAN) and/or a public network, for example, the Internet) through a network adapter 1240. As shown in FIG. 12, the network adapter 1240 communicates with other modules of the computing apparatus 1200 through the bus 1250. It should be understood that although not shown in the figure, other hardware and/or software modules may be used in conjunction with the computing apparatus 1200, including but not limited to: microcode, a device drive, a redundant processing unit, an external magnetic disk drive array, an RAID system, a magnetic tape drive, a data backup storage system, and the like.

The processor 1220 performs various functional applications and data processing by running the program stored in the storage device 1210, for example, implementing the method for generating an object structural model and a collision prediction method described in the embodiments of the present disclosure.

Program code may be implemented in a high-level procedural programming language or an object-oriented programming language so as to communicate with a processing system. If desired, the program code may also be implemented in an assembly language or a machine language. In fact, the mechanisms described herein are not limited to the scope of any particular programming language. In any case, the language may be a compiled language or an interpreted language.

Preferred embodiments of the present disclosure have been described in detail above. However, it should be understood that the present disclosure can employ various embodiments and variations without departing from the broad spirit and scope thereof. Those of ordinary skill in the art can make numerous modifications and variations according to the concept of the present disclosure without creative efforts. Therefore, all technical solutions that can be obtained by those skilled in the art through logical analysis, reasoning or limited experiments based on the prior art according to the concept of the present disclosure shall fall within the protection scope defined by the claims of the present disclosure.

The invention claimed is:

1. A method for generating an object 3D point cloud in a medical imaging system, wherein the medical imaging system comprises:
   a depth camera;
   a table for carrying an object; and
   a scanning device coupled to the table and the depth camera, the scanning device having a scanning space allowing the table to enter therein,
   the method comprising:
   generating a global 3D point cloud, wherein the global 3D point cloud includes an 3D point cloud of the object and a surrounding environment thereof;
   extracting a valid 3D point cloud in a valid region where the table is located from the global 3D point cloud based on a current height of the table and boundary information of the table obtained from real-time position information from the medical imaging system, wherein a bottom surface of the valid region is a carrying surface of the table, and the object 3D point cloud is comprised in the valid 3D point cloud;

reducing noise from the valid 3D point cloud by deleting points in a noise class; and removing an environment 3D point cloud of the surrounding environment from the valid 3D point cloud to obtain the object 3D point cloud, wherein the surrounding environment comprises at least part of the table.

2. The method according to claim 1, wherein the medical imaging system is a computed tomography (CT) system.

3. The method according to claim 1, wherein the boundary information of the table comprises position information of four corners of the table, and the valid region is rectangular.

4. The method according to claim 1, wherein a width of the valid region is greater than a maximum width of the scanning space in a width direction of the table.

5. The method according to claim 1, wherein a length of the valid region in a length direction of the table is greater than a length of the table.

6. The method according to claim 1, further comprising performing coordinate conversion on at least one of the global 3D point cloud and the boundary information of the table to convert them to the same coordinate system.

7. The method according to claim 6, wherein the same coordinate system is a coordinate system of the global 3D point cloud itself or a coordinate system of the medical imaging system.

8. The method according to claim 1, further comprising:
receiving depth image data of the object and the surrounding environment thereof from the depth camera; and
converting the depth image data into the global 3D point cloud through coordinate transformation.

9. The method according to claim 1, further comprising voxelizing the object 3D point cloud.

10. The method according to claim 1, wherein the environment 3D point cloud is pre-stored in the medical imaging system or obtained by photographing the surrounding environment using a depth camera before the object is carried on the table.

* * * * *